United States Patent [19]

Day et al.

[11] 4,187,858
[45] Feb. 12, 1980

[54] METHOD AND APPARATUS FOR ORIENTING THE DISPLAY OF INFORMATION FROM A RECIRCULATING MEMORY

[75] Inventors: Christopher C. Day, Newtonville; Robert A. McEachern, Wellesley, both of Mass.

[73] Assignee: American Optical Corporation, Southbridge, Mass.

[21] Appl. No.: 896,835

[22] Filed: Apr. 17, 1978

[51] Int. Cl.² .............................................. A61B 5/04
[52] U.S. Cl. ............................................... 128/710
[58] Field of Search ................ 128/2.06 A, 2.06 F, 128/2.06 G, 2.06 D, 419 A; 346/33 ME; 364/417

[56] References Cited
U.S. PATENT DOCUMENTS

| | | | |
|---|---|---|---|
| 3,587,564 | 6/1971 | Hagan et al. | 128/2.06 R |
| 3,718,772 | 2/1973 | Sanctuary | 128/2.06 A |
| 4,109,243 | 8/1978 | Day et al. | 346/33 ME |

*Primary Examiner*—William E. Kamm
*Attorney, Agent, or Firm*—Jeremiah J. Duggan; Alan H. Spencer; Stephen A. Schneeberger

[57] ABSTRACT

In apparatus such as a defibrillator having a CRT display of an ECG wave, and an alternative display of the firing time of the defibrillator pulse in relation to the ECG wave, the inclusion of method and apparatus for orienting the waveform to a synchronization indicator. In the preferred form, the display is a single, non-fade stationary complex of the ECG wave starting prior to the occurrence of the oriented "P" wave. The display is timed through combination of clocking pulses responsive to a wave detection apparatus and a recirculating memory which establishes an orienting marker. The clock pulsing includes a predetermined delay to initiation of display from the data recirculating memory such that the data display is coordinated in time to a fixed reference.

9 Claims, 5 Drawing Figures

METHOD AND APPARATUS FOR ORIENTING THE DISPLAY OF INFORMATION FROM A RECIRCULATING MEMORY

BACKGROUND OF THE INVENTION

This invention relates to electronic equipment for orienting the data trace from a recirculating memory to the display apparatus such that the otherwise "moving" trace becomes stationary on the display. Such apparatus is advantageously incorporated in apparatus for synchronously defibrillating a patient.

In defibrillators, electrical depolarizing impulses of high voltage are used to revert certain arrhythmias in the heart beat and thereby re-establish a more normal heart function. It is known that application of the depolarizing impulse at the wrong time of a beat cycle can cause cardiac arrest, thus, it is desirable to check the point in the cardiac cycle for the application of the defibrillating pulse. In order to check the cardiac cycle, an ECG display is utilized which will show the full waveform of the cardiac cycle. This waveform is normally comprised of a series of characteristic points conventionally designated by the letters P, Q, R, S and T. The Q, R and S portions of the wave, when taken together, are referred to as the QRS complex, or alternatively, the R-wave. Conventional methods and equipment for determining that the R-wave has occurred. An example of such detectors is disclosed in U.S. Pat. No. 3,590,811 issued July 6, 1971 for Electrocardiographic R-Wave Detector.

It has further been found that arrhythmias are preferably treated with the depolarizing impulse at a specific point of the ECG waveform. Therefore, a provision for verifying the trigger point on the ECG wave is often provided in defibrillator apparatus to view the point on the ECG waveform (R-wave) at which time the depolarizing pulse is delivered. This timing of the depolarizing pulse to fall on the proper segment of the ECG waveform is called "synchronizing" in the domain of defibrillating art.

It is conventional to utilize some electronic notation on the ECG cardiac waveform to indicate that point in the cardiac cycle in which the defibrillator or cardioverter is prescheduled to deliver its impulse. Previous techniques utilized vertical markers superimposed on the waveform all of which moved across the display face. We have found, however, that the utilization of such marks can, in fact, become merged into the R-wave in the ECG waveform causing confusion in interpreting the waveform and identifying the necessary synchronizing point.

Additionally, horizontal electronic markers have been used, however, these also are apt to be confusing in that their important time reference is at the intersection of the horizontal marker and the vertical trace.

Brightness marks or spots have additionally been utilized to provide a blip at the synchronizing point. We have found that these additionally cause problems in that there is a strong tendency at the level at which ECG waveform monitors are operated in defibrillating situations, for the spot merely to bloom the trace of the waveform and thus not readily identify the key point on the general trace. The tendency is to overdrive the cathode ray tube at this point and create a blur, washing out the entire waveform. One might suggest that the overall brightness of the display be lowered, however, such defibrillators are often used in brightly lit areas, such as outdoors, and the high brightness is necessary to see the waveform at all.

DESCRIPTION OF THE PRIOR ART

The present invention utilizes a CRT for writing data in an analog form which has been stored in a recirculating memory and is recalled to be displayed at a rate faster than that at which the data was initially collected. Additionally, the data is recirculated and updated through the memory and redisplayed such that the refresh rate of the data display is substantially greater than the decay time of the CRT phospher. Such displays are known to some in the art as "non-fade" CRT displays.

U.S. Pat. No. 3,406,387 illustrates a chronological trend CRT display utilizing a memory which is updated with current information. The data is stored in digital form and then converted to analog and supplied to the Y axis of the CRT.

U.S. Pat. No. 3,652,999 also illustrates a CRT data presentation system when analog data is converted, digitally stored on a repeating storer, converted back to analog information and displayed on the Y-axis of the CRT. The importance of this patent over the above-mentioned is the continuous drive of the Z-axis of the CRT rather than periodic blanking during the data feed time.

U.S. Pat. No. 3,886,950 is an illustration of a defibrillator for providing depolarizing impulses to a patient. Conventionally, such instruments also include combinations of features of ECG waveform analyzers and data displays disclosed in the above patents to additionally provide patient physiological information during cardioversion.

The above-cited references we believe to be representative of the state of the art.

SUMMARY OF THE INVENTION

Among the certain features of the present invention is the inclusion of an alternative display of a waveform with an event notation such as the synchronization of the defibrillation pulse to the ECG signal during a selected period of time. It is preferred that the display consists of a single, non-fade, stationary complex of the waveform such as the ECG wave starting at some time prior to the occurrence of the full waveform of interest (e.g., the "P" wave.) In this manner, the moment of event notation, or synchronization, may appear stationary in the display and be oriented to occur approximately in the middle of the display screen. With the notation or synchronization wave thus oriented, a clearly visible reticle can be oriented to indicate the precise event moment on the selected portion of the displayed wave. In the illustrated embodiment, a reticle is in the form of a graticule placed on the face of the cathode ray tube, however, a notation by the electronic beam may be more advantageously used than with the previous systems described since the wave is displayed stationary and the synchronization point can be more readily observed when noted with a small mark electronically placed. Electronic notation on an ECG wave is further enhanced since the ECG wave is caused to remain stationary on the face of the CRT for the duration of each beat so that its relationship to the stationary synchronization mark is readily observable.

DESCRIPTION OF THE DRAWING

FIG. 3b is an illustration of the waveform input and output of the circuit in 3a.

DESCRIPTION OF THE PREFERRED EMBODIMENT

Figure 1:
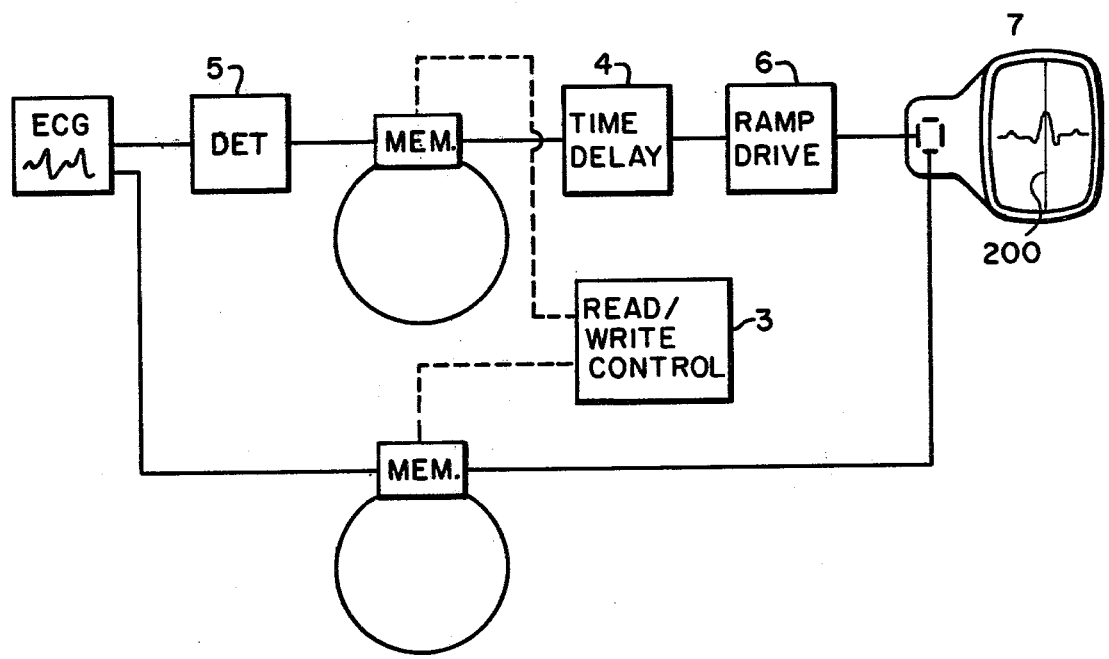
FIG. 1 is a diagrammatic illustration in block form of apparatus of the present invention.

Referring now to FIG. 1, the basic elements of the invention are illustrated. These include, in conjunction with conventional sensing and display apparatus, a recirculating marker memory 2 which may conventionally be a one-bit recirculating memory. Memory 2 being accessed through conventional read and write control 3 provides a marker or orienting mark to time delay 4. Data, an orientation marker, is input to the marker memory from an event detector 5 which may be a threshhold detector responding to a portion of a waveform. Time delay 4 provides a predetermined delay in the ramp drive 6 of data display 7 (e.g. a CRT) to initiate the ramp drive (X-axis) of the CRT oriented to begin its time base coordinated to the data to be recorded on display 7 such that a waveform of interest will be presented in total and in predetermined orientation. The data of the waveform is collected in a recirculating data memory 8 which, according to read and write control 3 supplies the digital/analog data to be recorded on display 7, on cue from the time-delayed orienting mark.

Figure 2:
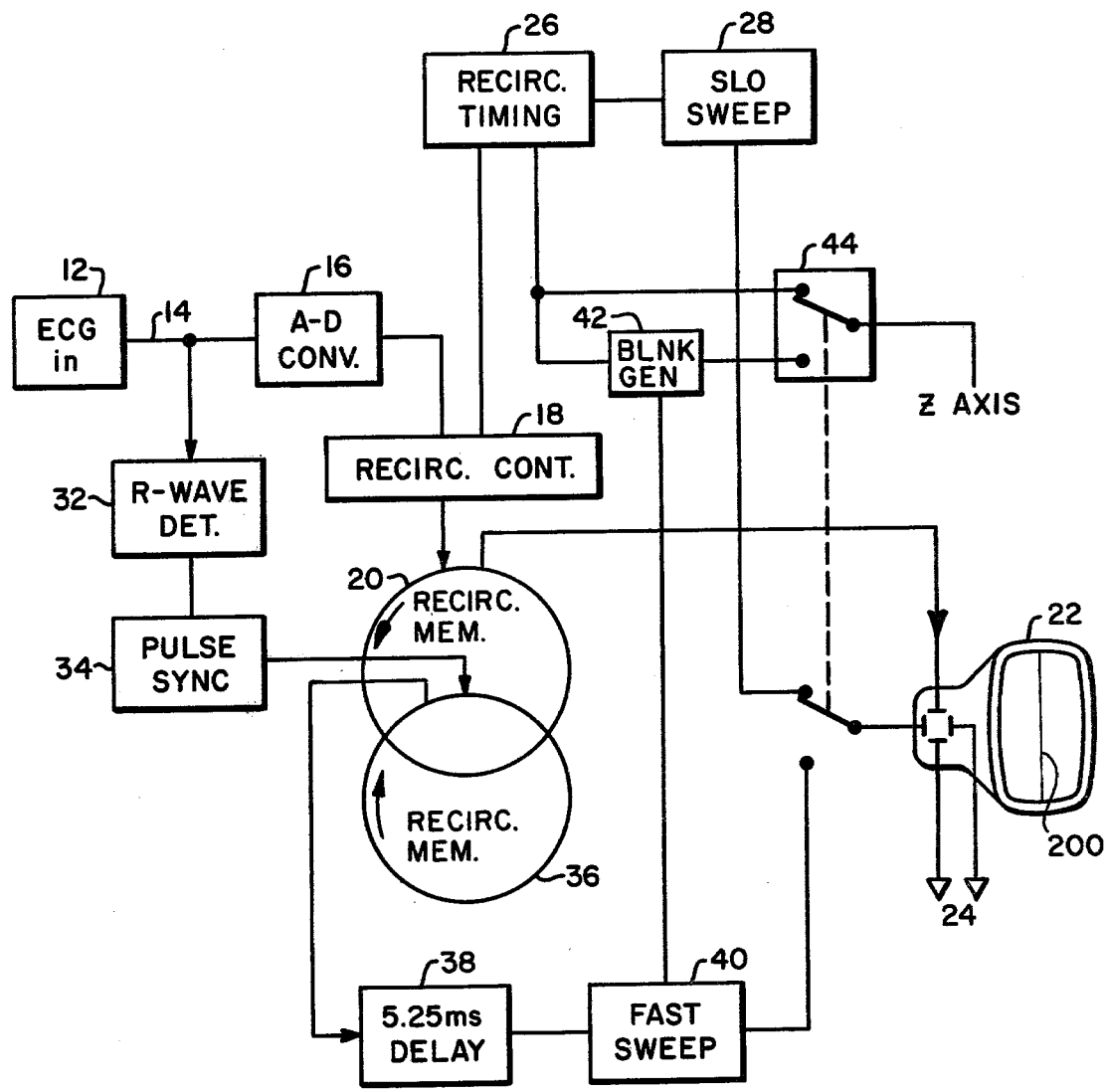
FIG. 2 is a diagrammatic illustration of a preferred embodiment of the invention of FIG. 1.

Referring now to FIG. 2, there is an illustration of the present invention being an adaptation of a digital CRT system which displays a precessing waveform and the present method and apparatus for synchronizing the defibrillation signal to a specific portion of the cardiac cycle as displayed on the CRT display.

FIG. 2 illustrates the inclusion of the present invention in a precessing waveform digital display system. In such a system, as illustrated in U.S. Pat. Nos. 3,745,407 and 3,768,093, assigned to the assignee of the present application, there is illustrated such precessing waveform digital CRT display systems. In such systems, an electrocardiographic signal (ECG) is generated in a patient on leads, as well known in the practice of cardiology. The signal is represented as generated in the box 12 labeled $ECG_{in}$. The signal is carried on conductor 14 to an analog to digital converter 16 and subsequently through recirculating control 18 into a recirculating memory 20 as described in the previously-identified publications. The stored signal is then extracted and applied to the CRT display 22 as being applied to electrodes 24 to modulate the Y-axis of the electron beam scan of the CRT tube. Further conventional elements of such a system are the recirculating timer 26, the sweep control 28, which are also described in the previously-identified publications.

Being included in the present embodiment are an R-wave detector 32, similar to those known in the art and illustrated in such as U.S. Pat. No. 3,590,811, also assigned to the assignee of the present application. Additionally, there is included a pulse synchronizer 34 which, in turn, controls the entry of a one-bit marker into such as a one-bit wide, recirculating memory 36 having a time length of the same length as memory 20. This pulse synchronizer and one-bit memory form part of an "orienting memory" which is essential to the invention to provide the new oriented display of waveform on the display apparatus (e.g. CRT). Responsive to the one-bit recirculating memory 36 is a predetermined time delay which in the present embodiment is a 5.25 millisecond delay 38, which, in turn, inputs to a ramp control or in the present embodiment, a fast sweep control 40 for the CRT display 22. Blanking is provided as a preferred addition to the invention through blanking generator 42 in the usual fashion for either the normal precessing display through the slow sweep generator 28 or for the orienting circuit described herein from the fast sweep generator 40. This is accomplished through a "Synchronization Test Switch" 44 which is instrumental in engaging the orienting circuit herein described. Full operation of this circuit will be described and illustrated subsequently.

Figure 3A:
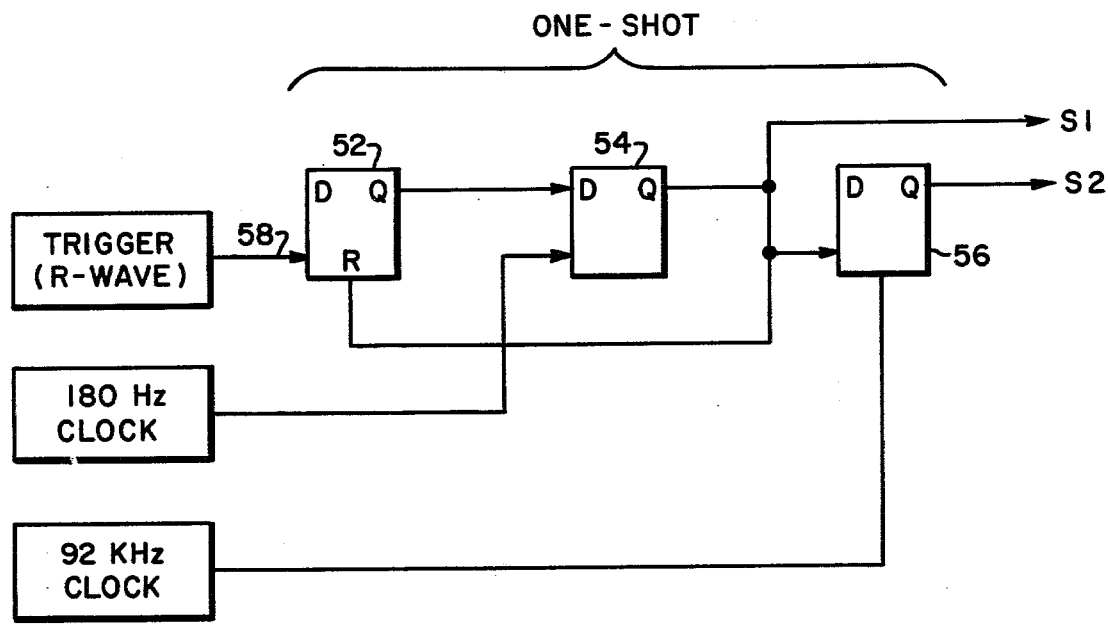
FIG. 3a is an illustration in block form of clocking for the wave synchronization of the invention.
Figure 3B:
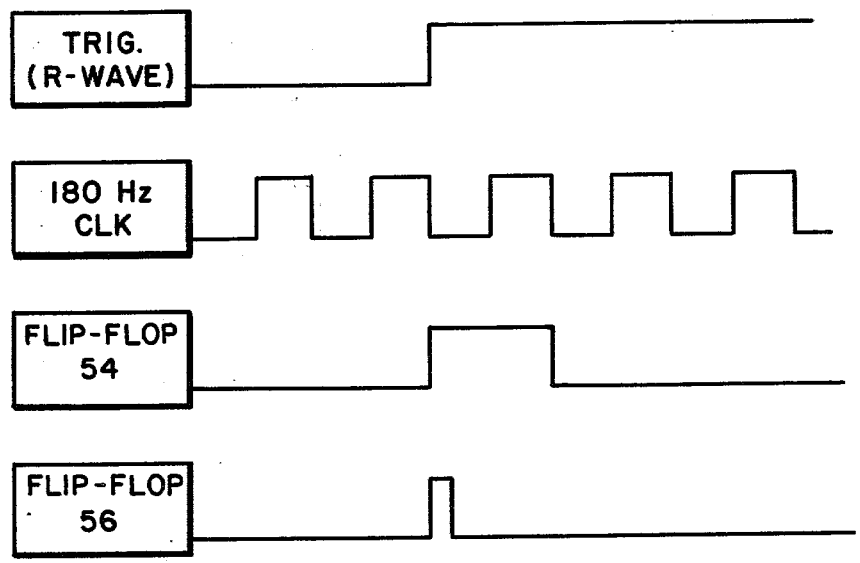

Referring now to FIG. 3a, pulse synchronization is accomplished in circuit element 34 of FIG. 2 in a standard synchronized one-shot technique by a series of clock functions in circuit elements, 52, 54, and 56. In the embodiment subsequently illustrated for synchronizing the R-wave of an ECG signal, 180 hertz and 92 KHz inputs are provided as indicated at flip-flops 54 and 56. Further, the pulse signal from the R-wave detector is provided at input 58. As illustrated in FIG. 3b, the combinations of clock pulses, the triggering signals S1 and S2 are provided. Signal S2 is utilized in the present circuitry as subsequently described in the generation of a synchronizing pulse. Output S1 is utilized to trigger the delay switch which, in the present embodiment is a 5.25 millisecond one shot. It is the output of the delay switch or one shot which initiates the ramp generator for the synchronizing signal display.

In summary then, the R-wave detector produces an indication of that portion of the EKG signal of interest when applying a depolarizing pulse. Through the utilization of appropriate clock circuitry, a synchronizing signal may be generated and stored for providing a later indication of that point in the overall EKG signal at which the R-wave detector makes its determination of the selected portion of the EKG signal. Further, the clock circuitry, through the utilization of a delay switch, may initiate a ramping at a known time after the first R-wave detection and determined to be prior to the beginning of the next full repetition of that R-wave. Thus the disclosed circuitry provides for a stationary presentation on the screen when activated such that the given EKG wave may be observed in detailed fashion and with reference to the synchronization marker such as reticle line 200 superimposed thereon for determination of that point in time of circuit operation at which a defibrilation would be initiated if the discharge were selected.

Figure 4:
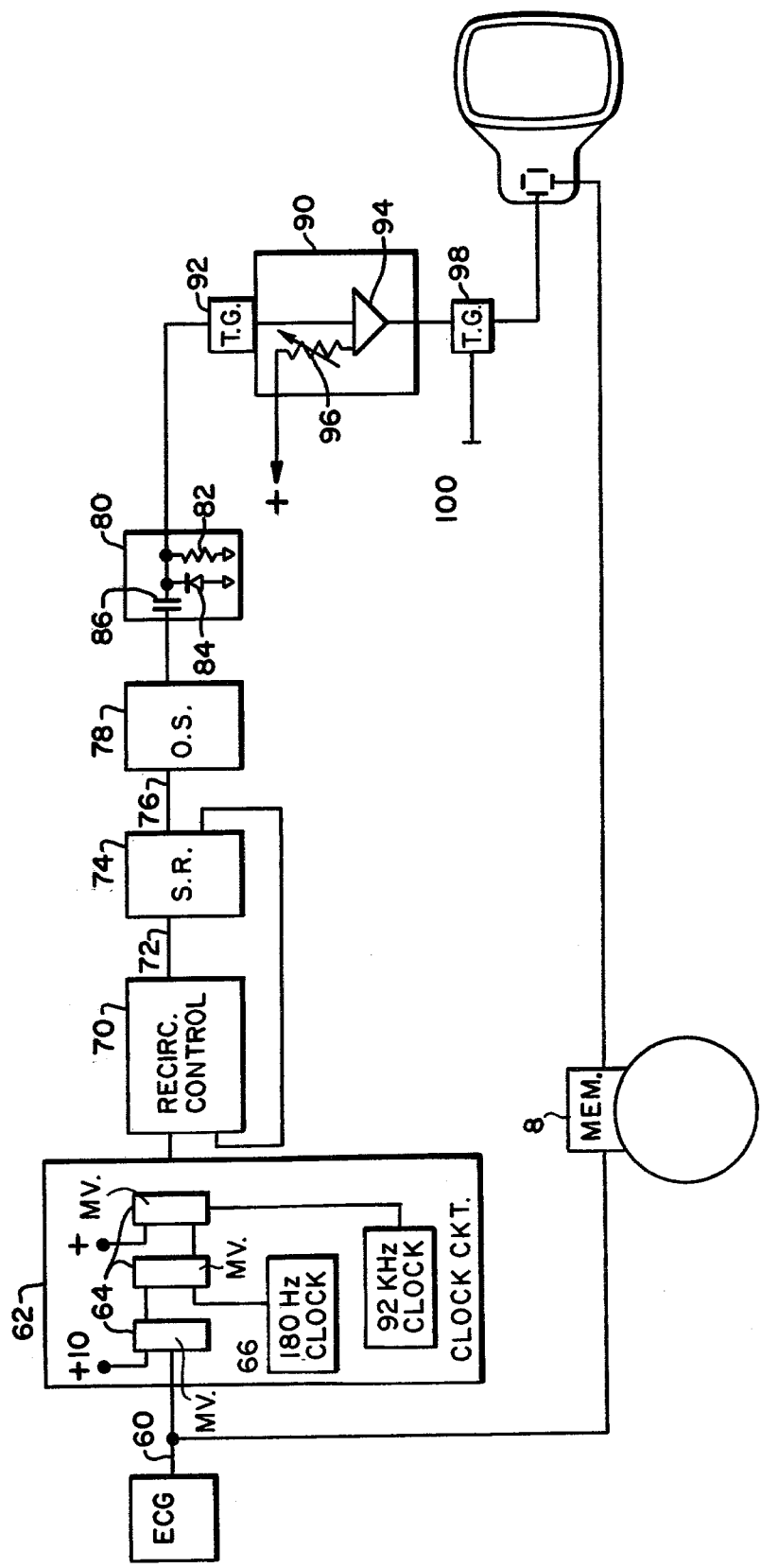
FIG. 4 is a detailed schematic of a preferred embodiment of the invention.

Referring now to FIG. 4, a specific circuit is illustrated which is satisfactory for providing the above-described display of defibrillator synchronization. FIG. 4 is to be interpreted as an improvement to ECG monitoring systems and displays and specifically those which incorporate means for synchronously defibrillating a patient. The standard ECG signal is supplied to the precircuit over conductor 60 to clock circuit 62 incorporating multivibrators 64 such as type No. 4013 available from RCA Corporation. This can be seen as the three multivibrators are interconnected and supplied with a 180-cycle supply 66 such that the train of pulses illustrated in FIG. 3 are produced. Output from the clocking circuit 62 is supplied over conductor 68 to a one-bit recirculation control 70 which may be a type of 4019 chip available from RCA Corporation. Recirculation control 70 outputs over conductor 72 to a one-bit shift register 74 such as a 2504-type available from Signetics Corporation which in turn outputs to the previously-described one shot 5.25 millisecond delay which may be a type 4047 available from RCA Corporation. The one shot 78 outputs through couplings circuit 80 which in the present circuit includes a 200 kilo ohm register 82, a catch diode 84 and a coupling capacitor of 0.001 microfarad value 86. The one shot then supplies the sweep circuit or ramp generator 90 upon which the ECG signal is orthogonally imposed. Circuits of this type are well known in the art. The present one includes transmission gate 92 to activate the circuit. Operational amplifier 94 of the type 308, available from National Semiconductor serves as the basic ramp generator. Variable resistance means 96 is used to bias the ramp generator to provide control for the left edge of the horizontal sweep signal or positioning of the ramp. A second transmission gate 98 is connected to the "sync test" control switch 100 which shifts the sweep drive to the horizontal of the CRT tube from the "sync test" sweep to the normal sweep and vice versa upon actuation of the "sync test" switch 100.

It should be thus realized that various adaptations and modifications of the present circuitry may be effected and still be recognized as within the elements, spirit and scope of the invention and thus coming within the meaning and range of equivalency of the claimed invention met as subsequently drawn.

We claim:

1. In apparatus having a recirculating memory means and a CRT means to display the ECG wave from a patient stored in the recirculating memory means, and means for detecting the R-wave of the ECG wave, the improvement comprising second recirculating memory means, clocking means responsive to the output of said R-wave detector to enter a single bit marker into said second recirculating memory means, time delay means responsive to said bit marker of said second memory means, the time delay of said time delay means corresponding to the predetermined interval prior to an upcoming full ECG wave, said time delay means outputting a trigger signal, and sweep circuit means responsive to said trigger signal for initiating the ramp signal applied to one axis of said CRT means.

2. The improvement according to claim 1 wherein said recirculating memory is one bit wide.

3. The improvement according to claim 1 wherein the length of said ramp signal is substantially single full ECG waveform.

4. In apparatus having a recirculating memory means and means for displaying data collected at one rate and displayed at a different rate, wherein the data is stored in said recirculating memory means, the improvement comprising means for detecting a predetermined portion of a repeating electrical signal, means fo noting the detection of said signal, means for storing said notation in a second recirculating memory, and time delay means responsive to said stored notation for outputting a sweep triggering signal, and sweep circuit means for displaying said stored data in response to initiation by said sweep triggering signal.

5. Apparatus including recirculating memory means for use in conjunction with apparatus for displaying data collected from a data source and storing said data in said recirculating memory means as a repeatable electrical signal for coordinating the display of said repeatable data signal to a subsequently determined event comprising; means for noting said event; means for storing said notation in said recirculating memory means; and time delay means responsive to said stored notation for outputting a sweep triggering signal, and sweep circuit means for displaying said repeatable data signal in response to initiation by said sweep triggering signal.

6. In apparatus having a recirculating memory means and a CRT means to display the ECG wave from a patient stored in the recirculating memory means, and means for detecting the R-wave of the ECG wave, the improvement comprising second recirculating memory means, means responsive to the output of said R-wave detector for entering a single bit marker into said second recirculating memory means in a predetermined constant time relation to the R-wave stored in said recirculating memory means, means responsive to a trigger signal for generating a ramp sweep signal applied to one axis of said CRT means, and means responsive to said bit marker of said second recirculating memory means for applying a trigger signal to said ramp signal generator to initiate a sweep a predetermined interval before the R-wave in the ECG wave stored in said first recirculating memory means thereby to substantially fix the position of the R-wave displayed on the CRT.

7. The improvement according to claim 6 wherein said ECG wave from a patient is entered into said recirculating memory means at a real-time rate and is displayed from said memory at a rate substantially faster than real-time.

8. The improvement according to claim 6 further including means defining a visible reference marker fixedly positioned on said CRT display means and wherein said predetermined interval by which said ramp triggering signal precedes the R-wave of the ECG in said recirculating memory means is selected to position a preselected part of the displayed ECG waveform at said visible reference marker.

9. The improvement according to claim 6 wherein said R-wave detector responsive means is operative to enter a said single bit marker in said second recirculating memory means in time coincidence with the R-wave of the ECG wave stored in said recirculating memory means, and said bit marker responsive means comprises time delay means for delaying the application of said trigger signal to said ramp signal generator relative to said single bit marker, said delay being preselected to apply said trigger signal at said predetermined interval before the R-wave of the ECG wave stored in the recirculating memory means.

* * * * *